(12) United States Patent
Poggio et al.

(10) Patent No.: US 6,231,735 B1
(45) Date of Patent: May 15, 2001

(54) OXYGEN LINEAR SENSOR TEST ARRANGEMENT

(75) Inventors: Luca Poggio, Spinetta Marengo; Marco Secco, Nizza Monferrato; Chiaffredo Rinaudo, Milan; Daniele Ceccarini, Rimini, all of (IT)

(73) Assignee: Magneti Marelli S.p.A., Milan (IT)

( * ) Notice: Subject to any disclaimer, the term of this patent is extended or adjusted under 35 U.S.C. 154(b) by 0 days.

(21) Appl. No.: 09/354,170

(22) Filed: Jul. 16, 1999

(30) Foreign Application Priority Data

Jul. 16, 1998 (IT) .............................................. BO98A0434

(51) Int. Cl.[7] .................................................. G01N 27/417
(52) U.S. Cl. ........................ 204/425; 204/406; 204/408; 123/693; 123/694
(58) Field of Search ..................................... 204/425, 426, 204/427, 428, 408, 406, 424; 123/693, 694, 696

(56) References Cited

U.S. PATENT DOCUMENTS

| | | |
|---|---|---|
| 4,532,013 | 7/1985 | Dietz et al. . |
| 4,796,587 * | 1/1989 | Nakajima et al. ................... 204/406 |
| 4,981,125 * | 1/1991 | Kato et al. ........................... 204/406 |
| 5,130,002 * | 7/1992 | Murase et al. ...................... 204/425 |
| 5,366,610 * | 11/1994 | Hirako et al. ........................ 204/406 |
| 5,524,472 | 6/1996 | Hötzel . |
| 5,558,752 | 9/1996 | Wang et al. . |

OTHER PUBLICATIONS

Patent Abstracts of Japan, 58–162858, Dec. 24, 1983.

* cited by examiner

Primary Examiner—Robert J. Warden, Sr.
Assistant Examiner—Kaj K. Olsen
(74) Attorney, Agent, or Firm—Venable; George H. Spencer; Robert Kinberg

(57) ABSTRACT

The control arrangement comprises an oxygen linear test sensor located along the exhaust duct of an internal combustion engine, the sensor having a chamber able to receive part of the exhaust gas and two electrolytic cells of which one is electrically piloted; the arrangement having a retro-operation test circuit able to adjust the current piloted to the cell to give rise to an oxygen ions draining mechanism from and/or towards the chamber which induces the stoichiometric condition within the chamber itself, and an outlet circuit able to convert the piloted current into a first signal representative of nature of the mixture fed to the engine; the arrangement being provided with a memory circuit which memorises the value of a compensation resistance of the eventual spreads of the piloted current of a correcting circuit receiving the stored value of the compensation resistance and able to ensure a correction for the first signal to recover the spreads of piloted current to the cell; the correcting circuit providing an outlet signal effectively representative of the nature and independent of the variations in compensation resistance.

8 Claims, 2 Drawing Sheets

OXYGEN LINEAR SENSOR TEST ARRANGEMENT

The present invention relates to an oxygen linear sensor test arrangement.

BACKGROUND OF THE INVENTION

In particular the present invention relates to the oxygen linear sensor test arrangement known as the "UEGO" sensor (universal exhaust gas oxygen sensor), to which the following makes explicit reference though without loss of its general nature.

The present invention is of advantage in the automotive field, where it is known to use a UEGO sensor, located along the exhaust manifold of an internal combustion engine, to obtain information concerning the composition of the exhaust gases.

The UEGO sensor has two electrolytic cells responding to oxygen ions, and a diffusion chamber placed between the actual cells and able to receive part of the combustion gases at the outlet from the engine. In addition, the UEGO sensor provides for the use of a test arrangement which is connected to the sensor itself by means of a connector, and is able to control electrically the electrolytic cells to produce a test action on the sensor itself. In particular such control means is designed to provide an oxygen ion draining mechanism from the diffusion chamber to atmosphere and vice versa, in order to obtain within the actual chamber an exhaust gas composition equal to that which would obtain in the event of the air/petrol ratio of the mixture fed to the engine becoming stoichiometric, i.e. equal to 14.57.

The intensity of the test action, that is to say the intensity of the pumping current required to maintain the stoichiometric level within the diffusion chamber, is the information on the basis whereof the test arrangement generates the Vout output signal representative of the composition of the exhaust gases proceeding from the engine. The Vout signal is proportional to the quantity of oxygen present within the exhaust gas and consequently, is indicative of the air stroke/petrol ratio of the mixture fed to the engine.

Presently the test arrangements, before installation on the vehicle, need to be connected to a compensation resistance to compensate for eventual spreads (variation) of the pumping current.

The compensation resistance, the nominal value whereof is shown by the sensor manufacturer on completion of production, is inserted between two connections of the said connector, and cooperating with the test arrangement, actively intervenes in the generation of the Vout signal. Unfortunately the compensation resistance, being located within the engine space, is subject to heavy thermal stresses during operation of the engine.

In consequence, on variation of the engine temperature it occurs that the compensation resistance assumes differing values in relation to the nominal value which would ensure a correct compensation. This means that the variation in pumping currents are not adequately compensated and that the control arrangement provides a Vout output signal which is not effectively indicative of the composition of the exhaust gases.

SUMMARY OF THE INVENTION

The purpose of the present invention is to achieve an oxygen linear sensor test arrangement, which provides a solution to the aforesaid problem. According to the present invention there is provided a control arrangement for an electrically controllable, linear oxygen sensor located along an exhaust manifold of an internal combustion engine and having a diffusion chamber for receiving part of the combustion gases of the internal combustion engine, the sensor having an output for supplying a first signal correlated with a difference between a composition of the combustion gases inside the chamber and a reference stoichiometric composition, the control arrangement comprising: a feedback control circuit having an input for receiving the first signal and for supplying a pumping current to the sensor to initiate an oxygen ion draining mechanism from and/or to the diffusion chamber for obtaining the reference stoichiometric composition inside the diffusion chamber; an output circuit for sensing the pumping current and for supplying a second signal in dependence of the pumping current correlated with a quantity of oxygen present in the combustion gases entering the diffusion chamber; a compensation resistance for compensating spreads of the pumping current between individual sensors: an acquisition circuit connected to the compensation resistance for producing a compensation parameter representative of the compensation resistance, the acquisition circuit comprising voltage supply means for supplying a reference voltage present at a first terminal of the compensation resistance, a voltage divider connected to a second terminal of the compensation resistance and having an output terminal supplying a voltage signal correlated with the compensation resistance, first and second analog to digital conversion means each having an input connected to a respective one of the voltage supplying means and the second terminal of said compensation resistance, calculation means having input terminals connected to respective output terminals of the first and second analog to digital conversion means for calculating and outputting the compensation parameter; storage means for storing the compensation parameter; and a correction circuit having inputs for receiving the compensation parameter and the second signal and having an output terminal supplying an output voltage correlated with the compensation parameter and with the second signal.

BRIEF DESCRIPTION OF THE DRAWINGS

The present invention is now described with reference to the appended drawings, which illustrate a non-restrictive operational example thereof, wherein.

DETAILED DESCRIPTION OF THE INVENTION

Figure 1:
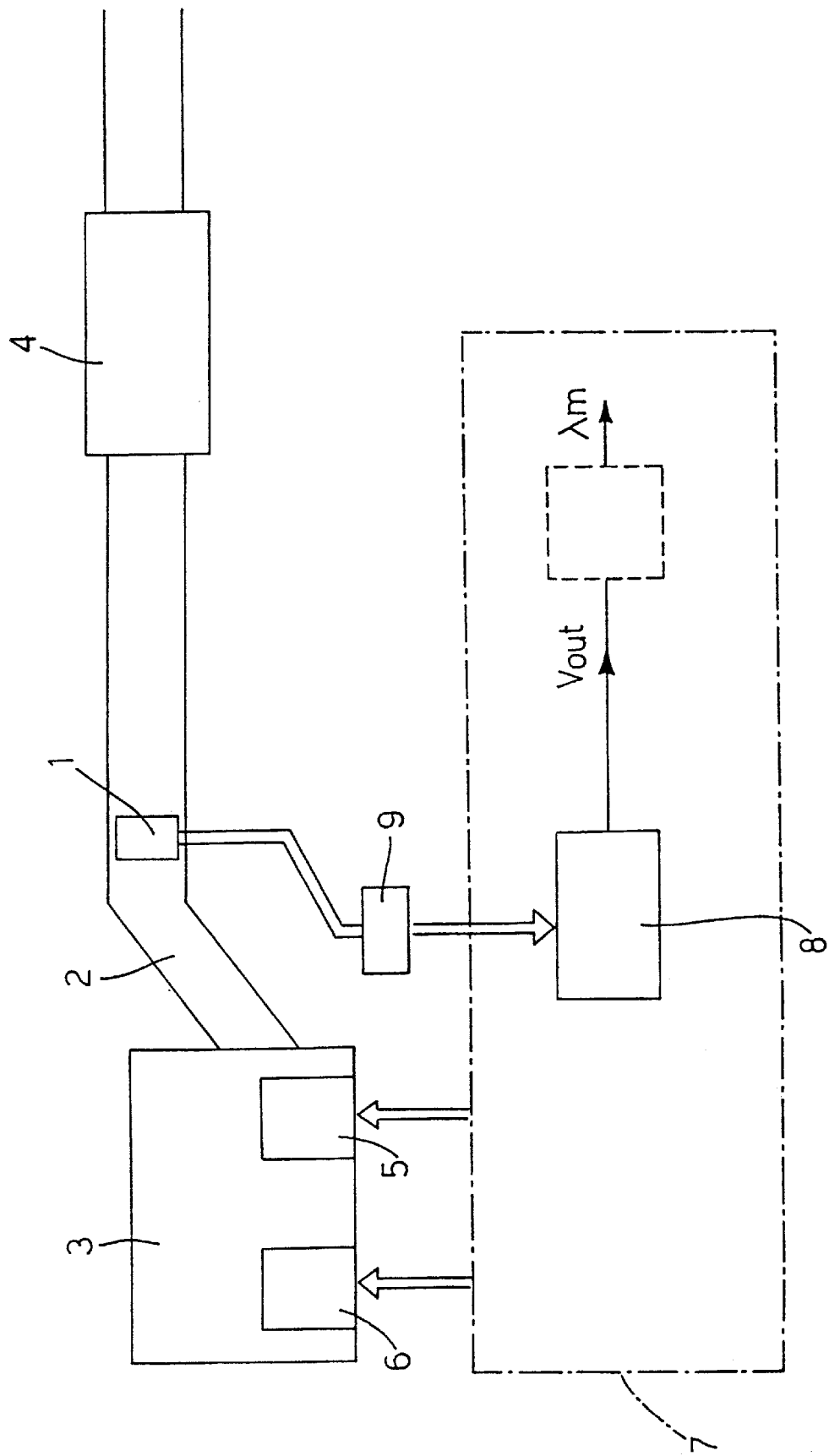
FIG. 1 illustrates diagrammatically the application of a UEGO sensor along the exhaust duct of an internal combustion engine.

With reference to FIG. 1, the reference 1 indicates a UEGO sensor of known type able to be located along the exhaust manifold 2 of an internal combustion engine 3 to obtain information concerning the stoichiometric composition of combustion gases, and finally concerning the A/F (air/fuel) ratio of the mixture supplied to the engine.

In the example illustrated here the sensor 1 is arranged upstream of a catalytic converter 4 able to reduce the polluting substances present in the combustion gases before they are ejected to external atmosphere.

The engine 3 has a fuel supply arrangement 5 (for instance using petrol) to the cylinders (not illustrated), and an ignition arrangement 6 to ignite the combustion processes within the cylinders. The engine 3 is controlled by an electronic central control unit 7 (illustrated diagrammatically) which controls the supply arrangement 5 to regulate the quantity of fuel to be injected into the cylinders, and controls the ignition arrangement 6 to regulate the ignition timing of combustion within the cylinders.

Figure 2:
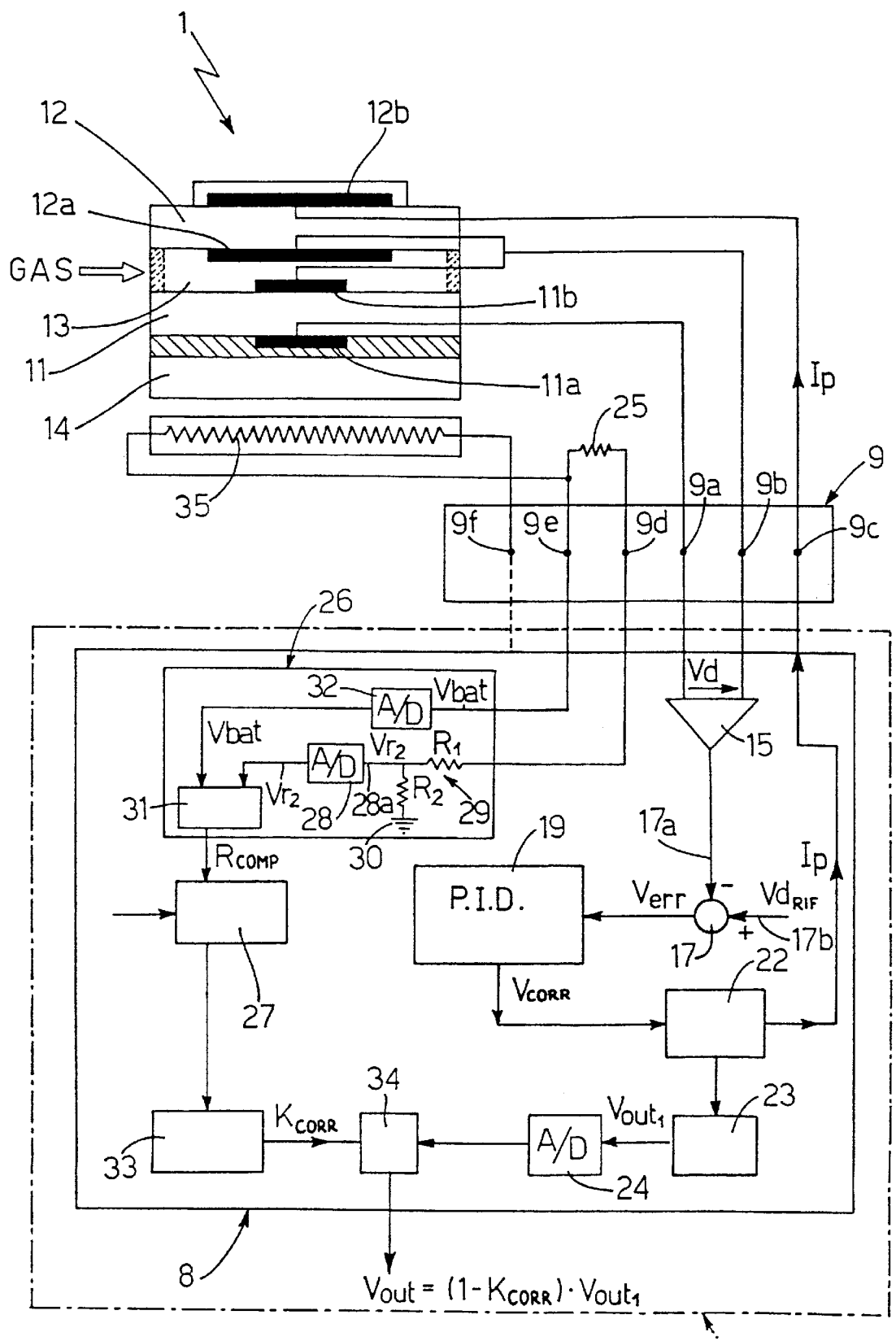
FIG. 2 illustrates diagrammatically a test arrangement for a UEGO sensor achieved according to the details of the present invention.

According to the present invention the electronic control unit 7 comprises an electronic control arrangement 8 for the UEGO sensor 1 which is connected to the sensor 1 by means of a connector 9. The control arrangement 8, as will be further specified later on, is able to process the information proceeding from the sensor 1 to generate a Vout output signal, which according to the present invention is a digital signal correlated with the quantity of oxygen present in the combustion gases and correlated with the A/F ratio. In particular, the Vout signal is the digital-converted result of a proportional analogue signal corresponding with the quantity of oxygen within the combustion gases. The Vout signal is thus determined by the central control unit 7, and in particular is converted (in a known manner) into a λm parameter representative of the air/fuel (A/F) ratio of the global mixture supplied to the engine 3 and defined as:

$$\lambda m = \frac{(A/F)\text{mis}}{(A/F)\text{stech}}$$

where (A/F)mis represents the value of measured air/fuel obtained by the sensor 1 and correlated with the Vout signal and with (A/F)stech as the value of the air/fuel stoichiometric ratio equal to 14.57. In particular, if the value of the λm exceeds unity (λm>1) the measured A/F ratio is greater than the A/F stoichiometric ratio and the mixture supplied to the engine 3 is said to be lean, whereas if the value of parameter λm is lower than unity (λm<1) the measured A/F ratio is lower than the A/F stoichiometric ratio and the mixture supplied to the engine 3 is said to be rich. FIG. 2 illustrates in greater detail the connection of the UEGO sensor 1 to the control arrangement 8 by means of the connector 9.

With reference to FIG. 2, the sensor 1 has two electrolytic cells 11 and 12 responding to oxygen ions, respectively termed "Vs sensing cell" and "pumping cell Ip", and a diffusion chamber 13 interposed between the cells 11 and 12 and able to receive the exhaust gas. The sensor 1 also has a reference chamber 14, which is located on the opposite side of the diffusion chamber 13 in relation to cell 11, and is in a stoichiometric condition, i.e. presenting an oxygen level equal to that which the exhaust gas would have in the event of the A/F ratio of the mixture fed to the engine being stoichiometric.

The cell 11 presents at its heads a pair of electrodes 11a and 11b electrically connected to respective connections 9a, 9b of the connector 9. In turn the cell 12 has at its heads a pair of electrodes 12a and 12b, of which the electrode 12a is connected electrically to the electrode 11b of cell 11, whereas electrode 12b is connected to a connection 9c of the connector 9. In service, between the connections 9a and 9b, that is to say at the heads of the sensing cell 11, there is a signal Vd (voltage) of which the value depends on the swing of the exhaust gas composition in the diffusion chamber 13 away from the stoichiometric level of the reference chamber 14.

The control arrangement 8, detailed below, has the dual function of electrical supply to the sensor 1 and ensuring a feedback control action designed to modify the composition of the gas in the diffusion chamber 13. In particular the arrangement 8 is able to control a pumping current Ip to the electrode 12b of cell 12 to achieve an oxygen ion draining mechanism in the diffusion chamber 13 out to atmosphere (and vice-versa) in such a way as to achieve a stoichiometric level within the diffusion chamber 13.

The control arrangement 8 generates the Vout output signal as a function of the intensity of the control action, that is to say the intensity of the pumping current Ip required to maintain a stoichiometric level within the diffusion chamber 13, is the information on the basis whereof the control arrangement 8 generates the output of Vout signal. According to the present invention, the control arrangement 8 comprises an amplifier 15 which is connected to the input of connections 9a and 9b of the connector 9 to receive the Vd signal (voltage), and is able to supply the amplified Vd signal to a subtracter input 17a of a summation node 17. In particular, the amplified signal Vd assumes values of around 450 mV whenever within the diffusion chamber 13 there are gases originating from the combustion of a stoichiometric mixture, and in the meantime assumes values greater than 450 mV (or respectively lower than 450 mV) when the gases originate from the combustion of a rich mixture (or respectively lean mixture).

The summation node 17 has a summation input 17b to which is supplied a reference signal $Vd_{RIF}$, which represents the reference (or set point) for the amplified Vd signal, and is equal to the amplified value of the signal Vd which is present at the heads of the cell 12 in the event that the exhaust gases emitted from the diffusion chamber 13 originate from the combustion of a stoichiometric mixture. In the example shown here, according to the afore-cited description, the reference signal $V_{dRIF}$ assumes the value 450 mV. The node 17 generates on its output an error signal Verr, which is defined by the difference between the reference signal $Vd_{RIF}$ and the amplified Vd signal, and is representative of the error between the voltage in the heads of cell 11 in the event of stoichiometric conditions and that which effectively is recorded at the heads of cell 12.

The error signal Verr is supplied to a processing circuit 19 which produces on its output a correction signal VCORR. In the illustrated example the processing circuit 19 is defined by a PID controller of known type able to effect a proportional integral derivative transformation (PID) of the Verr signal to generate the VCORR signal.

The VCORR correction signal is supplied to a control circuit 22 (of known type), which, on the basis of the VCORR signal, regulates the intensity of the pumping current Ip to be fed to cell 12. In particular, the VCORR signal is the input on the basis whereof the control circuit 22 corrects the Ip current so that the cell 12 drains the oxygen ions from the diffusion chamber 13 to atmosphere (or vice versa) to achieve stoichiometric conditions in chamber 13. In the example illustrated here the control circuit 22 is represented by a voltage/current converter of known type able to convert the VCORR voltage signal into a corresponding Ip current to be supplied to cell 12.

In this way a feedback control is achieved which tends to cancel the error signal Verr. According to the said feedback control, whenever the exhaust gases emitted by the diffusion chamber 13 are derived from combustion of a lean mixture, the Verr error signal is greater than zero, and the PID controls the control circuit 22 ;in order that within cell 12 a pumping current Ip is controlled such as to generate a flow of oxygen ions from chamber 13 to atmosphere. In that way by means of the feedback control, chamber 13 tends to be returned to a stoichiometric condition. And, vice versa, whenever the discharge gases are lower in oxygen, or are derived from combustion of a rich mixture, the error signal Verr is lower than zero, and the PID controls the control circuit 22 so that within cell 12 a pumping current Ip is controlled such as to generate a flow of oxygen ions from atmosphere into the diffusion chamber 13.

In addition, the control circuit 22, cooperates with an output circuit 23 which in a known manner, converts the pumping current Ip into an output Vout1 signal correlated with the composition of the combustion gases present in the discharge duct 2, or with the quantity of oxygen present in the gases leaving the engine 3. The output circuit 23 is thus able to convert the pumping current Ip supplied by the control arrangement 8 to maintain a stoichiometric condition in the diffusion chamber 13, into a $Vout_1$ signal, which is converted by the analogue/digital converter 24 into a digital signal Vout1 which but for a correction explained below, represents the Vout output signal from the arrangement 8.

According to the present invention the connector 9 has two further connections 9d, 9e (FIG. 2) between which a compensation resistance 25 is connected, and is able to allow compensation of eventual spreads (variation) in the pumping current Ip so that the Vout signal always remains indicative of the effective composition of the exhaust gases leaving the engine 3. The nominal value of the compensation resistance 25 is indicated for the purposes of manufacture of the sensor 1 and of the control arrangement 8 following functional tests carried out to check the efficiency of the sensor itself.

In other words, in the production of the sensor, to obtain a Vout signal which is effectively representative of the A/F ratio, it is necessary to take into consideration the spreads in pumping current Ip which could involve errors in the measurement of the A/F ratio of the mixture supplied to the engine. In consequence, the manufacturer will supply the value of a compensation resistance to be connected between two connections to interact with the output circuit 23 allowing recovery of the spreads.

According to the present invention, the control arrangement comprises a circuit 26 to acquire the resistance 25, which is connected to connections 9d and 9e, and cooperates with a storage circuit 27 (of known type) to allow permanent storage of a parameter Rcomp correlated with the compensation resistance 25. In particular, the storage circuit 27 stores the Rcomp parameter according to the engine ignition so that throughout the operation of the engine it is possible for compensation of the variation in Ip current always using the same parameter value Rcomp.

As illustrated in FIG. 2, in the acquisition circuit 26, connection 9e is supplied from resistance 25 with battery voltage Vbat, and allows the connection 9d to be connected to the input 28a of an analog/digital converter 28 by means of a voltage splitter 29. The splitter 29 has a resistance R1 connected between the connection 9d and input 28a, and a resistance R2 connected between the input 28a itself and earth 30. The analog/digital converter 28 thus receives on its input a voltage $Vr_2$ correlated with the value of the compensation resistance 25, and has an output connected to a calculator block 31 which also receives an input voltage Vbat from the battery by way of an analog/digital converter 32. The calculator block 31 is able to calculate the Rcomp parameter according to the expression $$Rcomp = \frac{R2 \cdot Vbat - Vr2(R1 + R2)}{Vr2}$$

wherein Vbat is the voltage of the acquired battery, $Vr_2$ is the output voltage of the converter 28, and R1 and R2 are splitter resistances 29.

The calculator block 31 thus supplies the Rcomp parameter to storage circuit 27.

The stored Rcomp parameter is supplied to an electronic panel 33 of known type, which has an output for supplying a correction KCORR parameter suitable for correcting the Vout1 signal to obtain the output signal Vout of arrangement 8. In particular in the example shown here, the KCORR parameter is combined with the $Vout_1$ signal, in a processing block 34 which has an output for supplying the Vout signal according to the expression:

Vout=$Vout_1 \cdot (1-K_{CORR})$

In this way, during the operation of the engine, the compensation of variations in the Ip current is effected with the same value of the Rcomp parameter and independently from the effective value assumed by the compensation resistance 25. In that way, even though resistance 25 is subjected to thermal stresses which might change the value in relation to the nominal value, the Vout signal remains independant of the changes in resistance 25 and always remains representative of the effective composition of the exhaust gases.

The storage of Rcomp parameter, which in the example illustrated here occurs following engine ignition, allows the $Vout_1$ signal always to be corrected with the same $K_{CORR}$ parameter, and therefore, obtaining a Vout output signal from the arrangement 8 that is not conditioned by changes in the compensation resistance 25.

As illustrated in FIG. 2, the sensor 1 also has a heating resistance 35 connected between the connection 9e and a further connection 9f of the connector 9 thereby allowing the maintenance of the sensor temperature within a predetermined temperature range (generally around 780° C.). In particular, the control arrangement 8 provides for a control unit (known and not illustrated) that regulates the current passing through the heating resistance 35 to rapidly take the temperature of the sensor within the predetermined temperature range upon ignition of the engine and to maintain the temperature of the sensor within that range throughout normal operation of the engine.

What is claimed is:

1. A control arrangement for an electrically controllable, linear oxygen sensor located along an exhaust manifold of an internal combustion engine and having a diffusion chamber for receiving part of the combustion gases of the internal combustion engine, the sensor having an output for supplying a first signal correlated with a difference between a composition of the combustion gases inside the diffusion chamber and a reference stoichiometric composition, the control arrangement comprising:

a feedback control circuit having: an input for receiving the first signal and for supplying a pumping current to the sensor to initiate an oxygen ion draining mechanism from and/or to the diffusion chamber for obtaining the reference stoichiometric composition inside the diffusion chamber;

an output circuit for sensing the pumping current and for supplying a second signal in dependence of the pumping current correlated with a quantity of oxygen present in the combustion gases entering the diffusion chamber;

a compensation resistance for compensating spreads of the pumping current between individual sensors;

an acquisition circuit connected to the compensation resistance for producing a compensation parameter representative of the compensation resistance, the acquisition circuit comprising voltage supply means for supplying a reference voltage present at a first terminal of the compensation resistance, a voltage divider connected to a second terminal of the compensation resistance and having an output terminal supplying a voltage signal correlated with the compensation resistance, first and second analog to digital conversion means each having an input connected to a respective one of the voltage supplying means and the second terminal of the compensation resistance, and calculation means having input terminals connected to respective output terminals of the first and second analog to digital conversion means for calculating and outputting the compensation parameter;

storage means for storing the compensation parameter; and a correction circuit having inputs for receiving the compensation parameter and the second signal and having an output terminal supplying an output voltage correlated with the compensation parameter and with the second signal.

2. Control arrangement according to claim 1, characterised in that the said storage means (27) are designed to store the compensation parameter (Rcomp) corresponding with a given moment, and are able to maintain in storage the stored compensation parameter (Rcomp) during the running of the engine (3).

3. Control arrangement according to claim 2, characterised by the fact that the storage means (27) are designed to store the compensation parameter (Rcomp) in accordance with the ignition of the engine (3).

4. Control arrangement according to claim 1, characterised in that the said correction circuit (33,34) comprises selection means (33) cooperating with the said storage means (27) to receive the stored compensation parameter (Rcomp) and select a correcting parameter (KCORR), and processing means (34) generating the output signal (Vout) according to the second signal (Vout1) and the correcting parameter; the said output signal (Vout) being independent of variations of the said compensation resistance (25) due to variations in the temperature of the engine (3).

5. Arrangement according to claim 4, characterised by the fact that it comprises analog-digital conversion means (24) receiving the said second signal ($Vout_1$) as input from the said output circuit (23) and able to supply to the correcting circuit (33,34) the second signal ($Vout_1$) in digitalized form.

6. Control arrangement according to claim 5, characterised by the fact that the said processing means (34) generate the said output signal (Vout) according to the expression $$Vout = Vout_1 \cdot (1 - K_{CORR})$$

wherein ($Vout_1$) is the said second digitalized signal and $K_{CORR}$ is the said correcting parameter.

7. Control arrangement according to claim 6, characterised by the fact that the said controller (19) is a controller of the P.I.D. type able to effect proportional-integral-derivative processing of the error signal (Verr).

8. Control arrangement according to claim 1, characterised by the fact that the said sensor (1) comprises at least a first (12) and a second electrolytic cell (11), of which the first cell (12) is able to be piloted through the said current (Ip) to vary the composition of the gas internally to the said diffusion chamber (13) be way of the said oxygen ion drainage mechanism from and/or to the chamber (13); the second cell (11) being able to supply the said first signal (Vd); the said control circuit in retroaction (15,17,19,22) comprising:

amplification means (15) able to amplify said first signal (Vd);

generation means for reference signal ($Vd_{ref}$) which is indicative of the value of the first amplified signal (Vd) in the event of the presence of the reference stoichiometric composition within the said diffusion chamber (13);

comparison means (17) allowing comparison of the said reference signal ($Vd_{ref}$) with the said first amplified signal (Vd), and to generate an error signal (Verr);

a piloting circuit (22) able to be controlled to pilot the said current (Ip) towards the said first cell (12); and a controller (19) receiving as input the said error signal (Verr) and able to carry out the processing of the error signal (Verr) to control as output the said piloting circuit (22) and thereby regulate said (Ip) current.

* * * * *